US00PP10136P

United States Patent [19]

Dümmen

[11] Patent Number: Plant 10,136

[45] Date of Patent: Dec. 2, 1997

[54] POINSETTIA PLANT NAMED 'DUESTAR'

[75] Inventor: Marga Dümmen, Rheinberg-Eversael, Germany

[73] Assignee: Dümmen Jungpflanzenkulturen, Rheinberg-Eversael, Germany

[21] Appl. No.: 672,713

[22] Filed: Jun. 28, 1996

[51] Int. Cl.[6] ..... A01H 5/00

[52] U.S. Cl. ..... Plt./86.4

[58] Field of Search ..... Plt./86.4

[56] References Cited

U.S. PATENT DOCUMENTS

P.P. 8,259 6/1993 Jacobsen ..... Plt./86.4

OTHER PUBLICATIONS

UPOV ROM Disk 1997/01 Search Report, 1996.

*Primary Examiner*—James R. Feyrer
*Assistant Examiner*—Kent L. Bell
*Attorney, Agent, or Firm*—C. A. Whealy

[57] ABSTRACT

A new and distinct cultivar of Poinsettia plant named 'Duestar', characterized by its bright red flower bracts; freely branching plant habit; compact plant habit; short crop time; large, showy reddish cyathia; and excellent postproduction longevity.

1 Drawing Sheet

The present invention relates to a new and distinct cultivar of Poinsettia plant, botanically known as *Euphorbia pulcherrima* Willd., named 'Duestar'. It is anticipated that the plant of this application will be marketed under the Trademark "HWD Starlight Dark Red". Accordingly, the plant of this application may be referred to as "HWD Starlight Dark Red" 'Duestar' in the market place.

The new cultivar is a product of a planned breeding program conducted by the inventor in Rheinberg, Germany. The objective of the breeding program was to develop freely branching red poinsettia varieties with excellent postproduction longevity.

The new cultivar is a spontaneous mutation of the commercial cultivar 'Beckmanns Altrosa', disclosed in U.S. Plant Pat. No. 9,336. The new cultivar was discovered and selected by the inventor in 1993 in a controlled environment in Rheinberg, Germany, as a single flowering plant among a population of plants of the parent cultivar 'Beckmanns Altrosa'. This single plant consistently formed inflorescences with red bracts compared to the pink-colored bracts of plants of the cultivar 'Beckmanns Altrosa'.

Asexual reproduction of the new cultivar by terminal cuttings taken at Rheinberg, Germany, has shown that the unique features of this new Poinsettia are stable and reproduced true to type in successive generations of asexual reproduction.

The following traits have been repeatedly observed and are determined to be the unique characteristics of 'Duestar'. These characteristics in combination distinguish 'Duestar' as a new and distinct cultivar:

1. Bright red flower bracts.
2. Freely branching plant habit.
3. Compact plant habit.
3. Short crop time, early to flower.
4. Large, showy reddish cyathia.
5. Excellent postproduction longevity.

The new cultivar can be compared to the commercial cultivar 'Angelika' (disclosed U.S. Plant Pat. No. 5,492). However in side-by-side comparisons conducted by the inventor in Rheinberg, Germany, the new cultivar differs from plants of the cultivar 'Angelika' in the following characteristics:

1. Plants of the new cultivar are shorter than plants of the cultivar 'Angelika'.

2. Plants of the cultivar 'Angelika' are more vigorous than plants of the new cultivar.
3. Leaves of the new cultivar are entire whereas leaves of the cultivar 'Angelika' are lobed.
4. Inflorescences and bracts of the new cultivar are smaller than inflorescences of the cultivar 'Angelika'.
5. Bract color of plants of the new cultivar is deeper red than bract color of plants of the cultivar 'Angelika'.
6. Nectaries of the new cultivar are scarlet in color compared to yellow nectaries of plants of the cultivar 'Angelika'.

A detailed comparison of the cultivars 'Duestar' and 'Angelika' appears in Chart A at the end of the specification.

The accompanying colored photograph illustrates the overall appearance of the new cultivar, showing the colors as true as it is reasonably possible to obtain in colored reproductions of this type. The photograph comprises a top perspective view of a typical potted plant of 'Duestar' with one pinched plant in a 15-cm container.

The cultivar 'Duestar' has not been observed under all possible environmental conditions. The phenotype may vary somewhat with variations in environment such as temperature, daylength and light intensity, without, however, any variance in genotype. The following observations, measurements and comparisons describe plants grown in Rheinberg, Germany, under commercial practice in a glass-covered greenhouse with day temperatures of 20° to 22° C. and night temperatures of 17° to 19° C. and light levels of 30 to 40 klux. Plants were grown in 15-cm pots with one pinched plant per pot. Short day treatments of 14 hours of dark were initiated two weeks after pinching. Spray applications of the growth retardant, chlormequat chloride, were given weekly from the start of short day treatment until bract coloration at a rate of 1500 ppm.

In the following description, color references are made to The Royal Horticultural Society Colour Chart except where general terms of ordinary dictionary significance are used.

Classification:

*Botanical.*—*Euphorbia pulcherrima* Willd.
*Commercial.*—Poinsettia.
*Cultivar.*—'Duestar'.

Parentage: Naturally occurring mutation of commercial cultivar 'Beckmanns Altrosa' (U.S. Plant Pat. No. 9,336).

Propagation:

*Type cutting.*—Terminal cuttings.

*Time to initiate roots.*—Summer: 25° C., 21 days. Winter: 18° to 20° C., 28 days.

*Rooting habit.*—Fine, freely branching.

Plant description:

*Plant form.*—Inverted triangle, top of plant rounded to flat.

*Growth habit.*—Freely branching and upright. Branching is enhanced by the removal of the apical shoot tip. Moderate growth rate and moderately vigorous. Relatively compact, suitable for 6 to 16-cm containers, most appropriate for 12.5 to 15-cm containers.

*Plant height.*—31 to 33 cm.

*Lateral branch length.*—22 to 24 cm.

*Crop time.*—From a rooted cuttings to a flowering plant in a 15-cm container, 12 weeks are required.

*Foliage description.*—Arrangement: Opposite. Quantity of leaves: 70 to 80 per flowering plant. Size: Length: 11 to 13 cm. Width: 7.5 to 8 cm. Shape: Ovate. Tip: Acute. Base: Obtuse. Margin: Entire. Texture: Upper side: Leathery, velvety, glabrous. Under side: Pubescent at veins. Color: Young foliage upper side: 137A. Young foliage under side: Greener than 147B. Mature foliage top side: 137A/137B. Mature foliage under side: Greener than 147B. Venation: Upper side: 146B/146C. Under side: 146D. Petiole: Length: 4.5 to 5 cm. Color: 183A on upper side fading to green, 147C, on underside.

Flower description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under short day/long night conditions.

*Time to flower.*—Eight weeks under short day/long night conditions.

*Quantity of inflorescences.*—7 to 8 per plant.

*Quantity of cyathia.*—12 to 17 per corymb.

*Inflorescence size.*—Diameter: 27 to 31 cm. Height (depth): 6 to 7 cm.

*Flower bracts.*—Attitude: Horizontal to stem axis. Quantity of flower bracts: 12 to 14 per inflorescence. Size: Length; 13 to 14 cm. Width: 7.5 to 8.5 cm. Shape: Ovate. Tip: Acute. Base: Obtuse. Margin: Entire, usually not lobed. Texture: Upper side: Smooth to slightly rugose, satiny, glabrous. Under side: Smooth to slightly rugose, satiny, glabrous. Color: When opening: Darker than 46B. Mature, top side: 46B with scarlet overtones. Mature, under side: 45C. Fading to: 45B. After senescence: 184B. Peduncle: Length: 2 to 4 mm. Color: 144B.

*Cyathia.*—Quantity: 12 to 17 per corymb. Diameter of cyathia cluster: 3 to 3.5 cm. Size, individual cyathia: Length: 1 to 1.5 cm. Width: 0.6 to 0.8 cm. Color: Immature: 144A. Mature: 144A/144B. Stamens: Stamen number: 20 to 30 per cyathium. Anther size: About 0.5 mm. Anther shape: Rounded. Anther color: 46A. Pollen color: 46A. Pistils: Pistil number: 1 per cyathium. Stigma: Shape: Trilobate. Color: 46A. Style: Length: About 2 mm. Color: 145B. Ovary number: 3. Nectaries: Usually one and sometimes two per cyathium. Color: Top of nectary, scarlet subtended by green, 144B.

Disease resistance: No fungal, bacterial nor viral problems observed.

Postproduction longevity: Generally more than 4 weeks under interior conditions.

CHART A

| CHARACTERISTIC | 'DUESTAR' | 'ANGELIKA' |
|---|---|---|
| PLANT HEIGHT | 31 to 33 cm | 37 to 40 cm |
| GROWTH RATE | Moderate | Rapid |
| VIGOR | Moderate | High |
| LATERAL BRANCH LENGTH | 22 to 24 cm | 27 to 30 cm |
| YOUNG LEAF COLOR, UPPER SIDE | 137A | 137C |
| YOUNG LEAF COLOR, UNDER SIDE | Greener than 147B | Lighter than 137C |
| MATURE LEAF COLOR, UPPER SIDE | 137A/137B | 137A/137B |
| MATURE LEAF COLOR, UNDER SIDE | Greener than 147B | Greener than 147B/147C |
| LEAF MARGIN | Entire | Lobed |
| LEAF LENGTH | 11 to 13 cm | 12 to 14 cm |
| LEAF WIDTH | 7.5 to 8 cm | 8.5 to 10.5 cm |
| INFLORESCENCE DIAMETER | 27 to 31 cm | 34 to 36 cm |
| BRACT LENGTH | 13 to 14 cm | 15 to 17 cm |
| BRACT WIDTH | 7.5 to 8.5 cm | 9 to 10 cm |
| BRACT COLOR WHEN OPENING | Darker than 46B | 45B |
| MATURE BRACT COLOR, UPPER SIDE | 46B with scarlet overtones | 45C |
| MATURE BRACT COLOR, UNDER SIDE | 45C | 46C/46D |
| BRACT COLOR, FADING TO | 45B | 46D |
| NUMBER OF BRACTS PER CORYMB | 12 to 14 | 12 to 16 |
| CYATHIA COLOR, IMMATURE | 144A | 144B |
| CYATHIA COLOR, MATURE | 144A/144B | 144C |
| NUMBER OF CYATHIA PER CORYMB | 12 to 17 | 10 to 15 |
| DIAMETER OF CYATHIA CLUSTER | 3 to 3.5 cm | 3.5 to 4 cm |
| NECTARY COLOR | Scarlet | Yellow |

It is claimed:

1. A new and distinct cultivar of Poinsettia plant named 'Duestar', as illustrated and described.

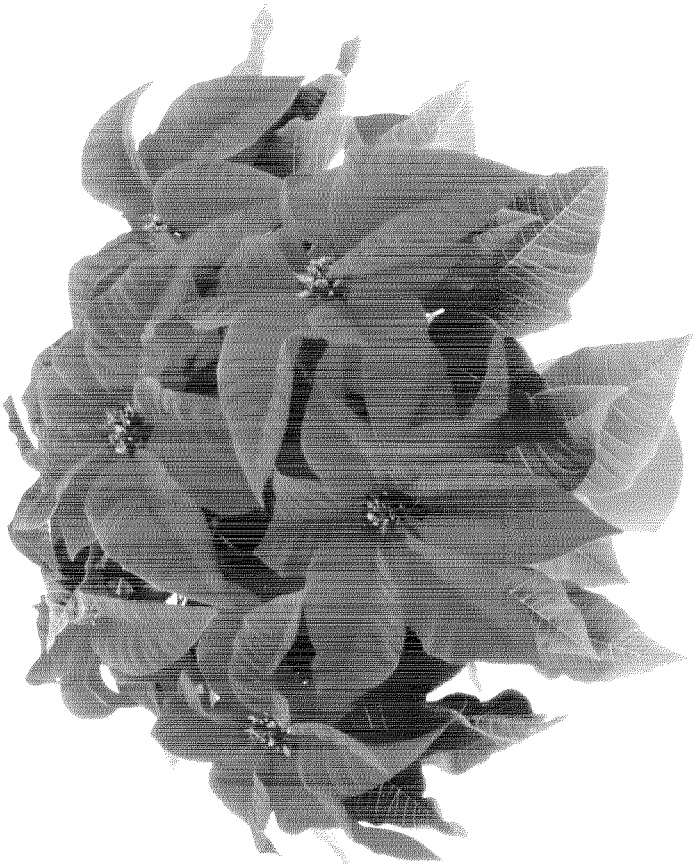

* * * * *